(12) United States Patent
Hamamatsu et al.

(10) Patent No.: US 7,903,244 B2
(45) Date of Patent: Mar. 8, 2011

(54) METHOD FOR INSPECTING DEFECT AND APPARATUS FOR INSPECTING DEFECT

(75) Inventors: Akira Hamamatsu, Yokohama (JP);
Minori Noguchi, Mitsukaido (JP);
Hidetoshi Nishiyama, Fujisawa (JP);
Yoshimasa Ohshima, Yokohama (JP);
Takahiro Jingu, Takasaki (JP); Sachio Uto, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/555,530

(22) Filed: Sep. 8, 2009

(65) Prior Publication Data
US 2009/0323054 A1    Dec. 31, 2009

Related U.S. Application Data

(63) Continuation of application No. 11/770,217, filed on Jun. 28, 2007, now Pat. No. 7,586,594, which is a continuation of application No. 10/724,750, filed on Dec. 2, 2003, now Pat. No. 7,248,352, which is a continuation-in-part of application No. 10/722,531, filed on Nov. 28, 2003, now Pat. No. 7,315,363.

(30) Foreign Application Priority Data

Nov. 29, 2002 (JP) ................................. 2002-347134
Dec. 2, 2002 (JP) ................................. 2002-349357

(51) Int. Cl.
*G01N 21/00* (2006.01)

(52) U.S. Cl. .................. 356/237.1; 356/237.2; 356/237.5

(58) Field of Classification Search ..... 356/237.1–237.5
See application file for complete search history.

(56) References Cited

U.S. PATENT DOCUMENTS

| | | |
|---|---|---|
| 3,658,420 A | 4/1972 | Axelrod |
| 3,790,280 A | 2/1974 | Heinz et al. |
| RE33,956 E | 6/1992 | Lin et al. |

(Continued)

FOREIGN PATENT DOCUMENTS

JP        59-204820        11/1984

(Continued)

OTHER PUBLICATIONS

Japanese Office Action dated Mar. 27, 2007.

*Primary Examiner* — Michael P Stafira
(74) *Attorney, Agent, or Firm* — Antonilli, Terry, Stout & Kraus, LLP.

(57) ABSTRACT

The present invention is an apparatus for inspecting foreign particles/defects, comprises an illumination optical system, a detection optical system, a shielding unit which is provided in said detection optical system to selectively shield diffracted light pattern coming from circuit pattern existing on an inspection object and an arithmetic processing system, wherein said shielding unit comprises a micro-mirror array device or a reflected type liquid crystal, or a transmission type liquid crystal, or an object which is transferred a shielding pattern to an optical transparent substrate, or a substrate or a film which is etched so as to leave shielding patterns, or an optical transparent substrate which can be changed in transmission by heating, sudden cold, or light illumination, or change of electric field or magnetic field, or a shielding plate of cylindrical shape or plate shape.

2 Claims, 21 Drawing Sheets

U.S. PATENT DOCUMENTS

| | | | |
|---|---|---|---|
| 5,463,459 | A | 10/1995 | Morioka et al. |
| 5,506,676 | A | 4/1996 | Hendler et al. |
| 5,854,674 | A | 12/1998 | Lin |
| 5,982,483 | A | 11/1999 | Lauinger et al. |
| 6,031,607 | A | 2/2000 | Miyazaki |
| 6,078,386 | A | 6/2000 | Tsai et al. |
| 6,404,498 | B1 | 6/2002 | Maeda et al. |
| 6,411,377 | B1 * | 6/2002 | Noguchi et al. ........... 356/237.4 |
| 6,686,995 | B2 | 2/2004 | Wilk et al. |
| 7,037,735 | B2 * | 5/2006 | Noguchi et al. ................ 438/18 |
| 2001/0019411 | A1 * | 9/2001 | Nara et al. .................... 356/394 |
| 2002/0154303 | A1 | 10/2002 | Maeda et al. |
| 2002/0176074 | A1 | 11/2002 | Hasan |
| 2003/0058436 | A1 * | 3/2003 | Ono et al. .................. 356/237.2 |

FOREIGN PATENT DOCUMENTS

| | | |
|---|---|---|
| JP | 62-089336 | 4/1987 |
| JP | 1-117024 | 5/1989 |
| JP | 1-250847 | 10/1989 |
| JP | 02-134265 | 5/1990 |
| JP | 05-093696 | 4/1993 |
| JP | 5-218163 | 8/1993 |
| JP | 6-258239 | 9/1994 |
| JP | 6-324003 | 11/1994 |
| JP | 8-210989 | 8/1996 |
| JP | 09-043160 | 2/1997 |
| JP | 09-213756 | 8/1997 |
| JP | 09-281324 | 10/1997 |
| JP | 11-352075 | 12/1999 |
| JP | 2000-105203 | 4/2000 |

* cited by examiner

CLOCKWISE TWINING SPRING - CLOCKWISE TWINING SPRING

CLOCKWISE TWINING SPRING - UNCLOCKWISE TWINING SPRING

Fig. 4
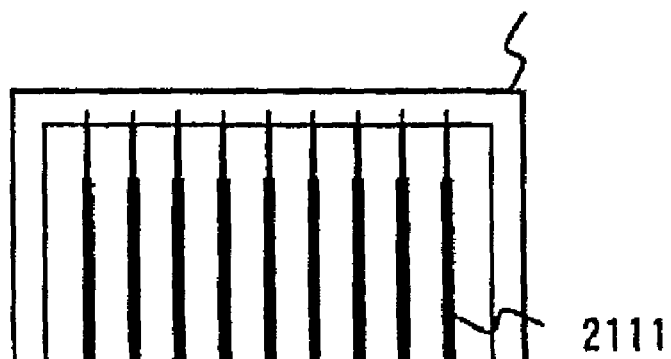
2110
2111
ENLARGEMENT
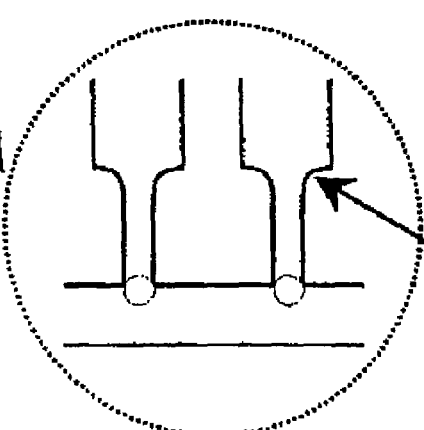
CURVATURE FORMATION

Fig. 7
| | TRANSMISSION TYPE LIQUID CRYSTAL | MIRROR ARRAY DEVICE |
|---|---|---|
| OPENING RATE / TRANSMISSION RATE | ✗ LOW OPENING RATE<br>✗ POLARIZATION NECESSITY<br>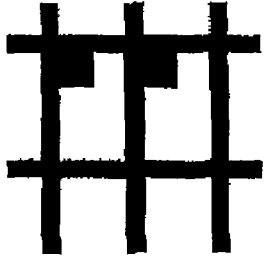 | ◯ HIGH OPENING RATE<br>◯ POLARIZATION NEEDLESSNESS<br>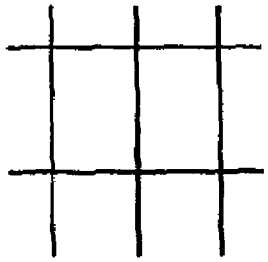 |
| COMPOSITION OF OPTICAL SYSTEM | ◯ TRANSMISSION<br>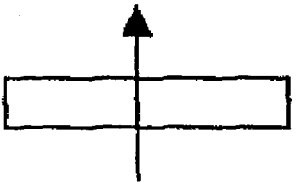 | ✗ REFLECTION OPTICAL SYSTEM NECESSITY<br>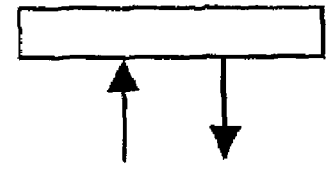 |

| | AREA A | AREA B | AREA C | AREA D |
|---|---|---|---|---|
| DIFRACTION PATTERN | 21 | 22 | 23 | 24 |
| OPTIMAL SHIELDING PATTERN | 31 | 32 | 33 | 34 |

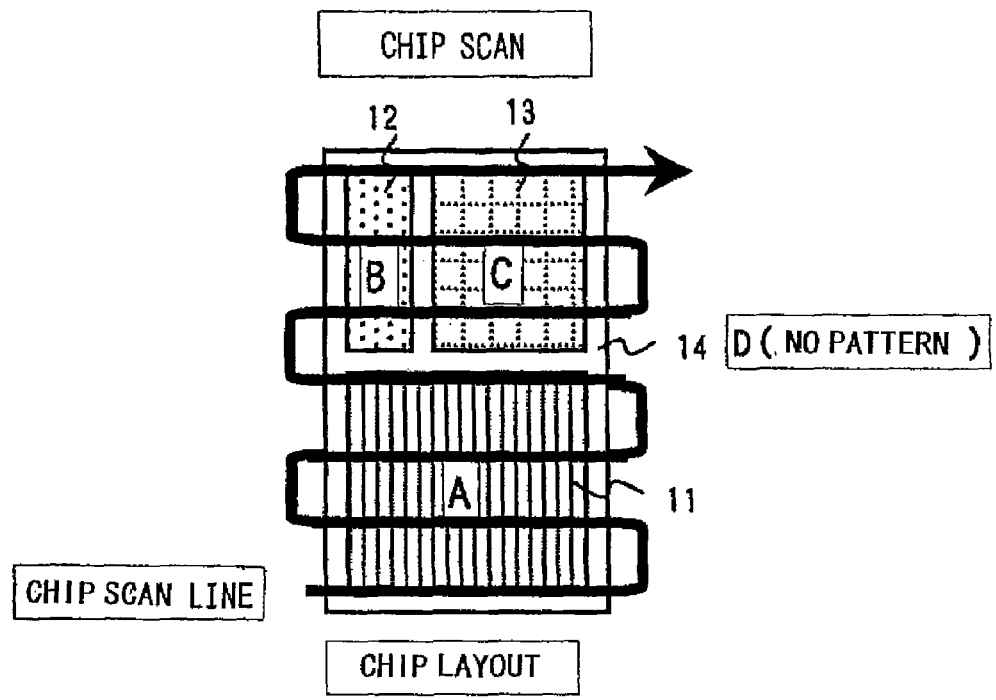

DIFFRACTION PITCH (P) BEING
CALCULATED FROM PATTERN PITCH (d)  $p = \dfrac{f \cdot \lambda}{d}$

METHOD FOR INSPECTING DEFECT AND APPARATUS FOR INSPECTING DEFECT

CROSS REFERENCE TO RELATED APPLICATION

This application is a Continuation of U.S. application Ser. No. 11/770,217, filed Jun. 28, 2007, now U.S. Pat. No. 7,586,594, which is a Continuation of U.S. application Ser. No. 10/724,750, filed Dec. 2, 2003, now U.S. Pat. No. 7,248,352, which claims priority from Japanese Patent Application No. JP 2002-347134, filed in Japan on Nov. 29, 2002, and Japanese Patent Application No. JP 2002-349357, filed in Japan on Dec. 2, 2002, and is a Continuation-In-Part of U.S. application Ser. No. 10/722,531, filed Nov. 28, 2003, now U.S. Pat. No. 7,315,363, which claims priority from Japanese Patent Application No. JP 2002-347134, filed in Japan on Nov. 29, 2002, and also relates to U.S. application Ser. No. 11/605,239, filed Nov. 29, 2006, now U.S. Pat. No. 7,586,593, which is a Continuation of U.S. application Ser. No. 10/722,531, filed Nov. 28, 2003, now U.S. Pat. No. 7,315,363, the contents of which are incorporated herein by reference.

BACKGROUND OF THE INVENTION

The present invention relates to a method for inspecting defect and an apparatus for inspecting defect in a production line for a semiconductor device, liquid crystal, magnetic head, or other device, and more particularly to a technology for inspecting foreign matters (particle)/defects existed on a processing substrate formed circuit patterns.

An example of semiconductor wafer inspection will now be described.

In a conventional semiconductor manufacturing process, any foreign matter existing on a semiconductor substrate (wafer) may cause a wiring insulation failure, short circuit, or other failure. Furthermore, since the semiconductor elements have turned minutely, when a fine foreign matter exists in the semiconductor substrate, this foreign matter causes for instance, insulation failure of capacitor or destruction of gate oxide film or etc. These foreign matters are mixed in the semiconductor substrate by various causes in the various state. As a cause of generating of the foreign matters, what is generated from the movable part of conveyance equipment, what is generated from a human body and the thing by which reaction generation was carried out by process gas within processing equipment, the thing currently mixed in medicine or material used can be considered. A liquid-crystal display device will become what cannot be used, if a foreign matter mixes on a circuit pattern or a certain defect produces a liquid-crystal display device manufacturing process similarly. The situation of the same is said of the manufacturing process of a printed circuit board, and mixing of the foreign matter becomes the short circuit of a pattern, and the cause of poor connection.

A certain conventional technology for detecting the above-mentioned foreign matters (particles) on a semiconductor substrate, which is disclosed, for instance, by Japanese Patent Laid-open No. 62-89336, illuminates laser light to the semiconductor substrate, detects the light scattered from any foreign matter on the semiconductor substrate, and compares the obtained result against the inspection result of the last inspected semiconductor substrate of the same type to conduct a high-sensitivity, high-reliability, foreign matter/defect inspection while averting a pattern-induced false alarm.

As one of the technology which detects the foreign matter on this conventional kind of semiconductor substrate, as indicated by a prior art 1 (Japanese Patent Laid-open No. 5-218163), loses the misreport by the circuit pattern, and it enables inspection of the foreign matter with the defect high sensitivity and the high reliability, by illuminating laser beam to the semiconductor substrate, detecting the scatter light generated from the foreign matter when the foreign matter is adhered on the semiconductor substrate and comparing with the inspection result of the semiconductor substrate of the same kind inspected immediately before.

Moreover, one of technology of inspecting the above-mentioned foreign matter is known a method for illuminating coherent light to the wafer, removing the light ejected from the repetition circuit pattern on the wafer by a spatial filter, and emphatically detecting the foreign matter and the defect without repetition nature. The foreign matter inspection apparatus which illuminates light from a direction angled 45 degrees for the main straight line groups of this circuit pattern to the circuit pattern formed on the wafer and does not input 0-order diffraction light from main straight line groups into an opening (a pupil) of an objective lens, is known by a prior art 2 (Japanese Patent Laid-open No. 1-117024).

Prior arts relating with an apparatus and a method for inspecting the defect of the foreign matter or the like are known as a prior art 3 (Japanese Patent Laid-open No. 1-250847), a prior art 4 (Japanese Patent Laid-open No. 6-258239), a prior art 5 (Japanese Patent Laid-open No. 6-324003), a prior art 6 (Japanese Patent Laid-open No. 8-210989) and a prior art 7 (Japanese Patent Laid-open No. 8-271437).

SUMMARY OF THE INVENTION

As indicated on the prior arts, on an apparatus for inspecting various kinds of minute circuit patterns including semiconductor device, although spatial filtering is separated efficiently between the signal being generated from the defect and the signal (pattern noise) being generated from the circuit pattern, number of diffraction light being generated from the pattern which can shield was restricted since the shielding plate with wide width was used from the problem of mechanical accuracy.

An object of the present invention can detect a foreign matter defect in high sensitivity by highly precise spatial filtering, on a technology for inspecting the minute (fine) circuit pattern by using images being formed by illuminating white light, single wavelength light or laser light to the minute (fine) circuit pattern.

In order to attain the object, the present invention is provided (1) a micro-mirror array device or a reflected type liquid crystal, or (2) a transmission type liquid crystal, or (3) an object which is transferred a shielding pattern to an optical transparent substrate, or (4) a substrate or a film which is etched so as to leave shielding patterns, or (5) an optical transparent substrate which can be changed in transmission by heating, sudden cold, or light illumination, or change of electric field or magnetic field, or (6) a shielding plate of cylindrical shape or plate shape.

In order to attain the another object, the present invention is provided a function which is changed the shielding pattern according to pattern change of diffraction light resulting from the difference in the form for every place of the circuit pattern which exists on the surface of the inspection object.

In order to attain the further another object, the present invention is provided a function which is changed according to at least two or more diffraction light patterns in pattern change of diffraction light resulting from the difference in the form for every place of the circuit pattern which exists on the surface of the inspection object.

BRIEF DESCRIPTION OF THE DRAWINGS

FIG. 4 is a front view showing an etching plate.

FIG. 7 is a comparison diagram of the transmission type liquid crystal and the micro mirror array device.

FIG. 20 is a plane view of a tip showing scanning path example of one tip (one die) which an image sensor is imaged.

FIG. 21 is the figure showing diffraction patterns for each area and correspondence position relations in the tip.

DETAILED DESCRIPTION OF THE PREFERRED EMBODIMENTS

Preferred embodiments of the present invention will now be described with reference to the accompanying drawings.

Figure 1:
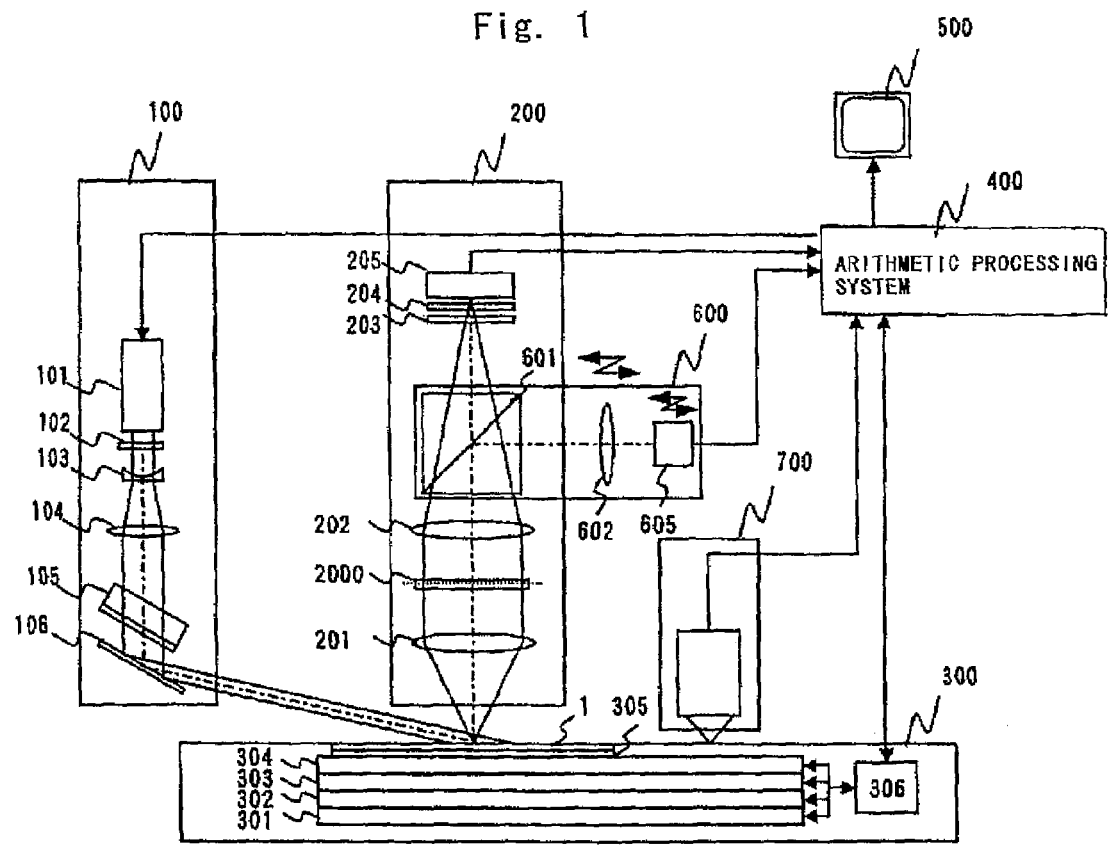
FIG. 1 is a front view showing an outline composition of an inspection apparatus which used a spatial filtering.

FIG. 1 is a schematic diagram illustrating one embodiment of an inspection apparatus according to the present invention. This inspection apparatus is suitable for inspecting foreign matters and defects. As shown in the figure, the inspection apparatus comprises an illumination system unit 100, a detection optical system unit 200, a stage system 300, an arithmetic processing system 400, a wafer observation unit 500 (monitor 500), a Fourier transform plane observation optical unit 600, and a wafer observation optical system 700. The illumination system 100 comprises a laser oscillator 101, a wavelength plate 102, beam expanders 103, 104 for varying the laser spot size, an aperture diaphragm 105 and a cylindrical lens 106. The wavelength plate 102 varies the degree of illumination light polarization. The beam expanders 103, 104 vary the illumination size (illumination area). A mirror (not shown) varies the illumination angle. The cylindrical lens 106 is used to illuminate an object under inspection with one side reduced.

The illumination system unit 100 is illuminated a slit-shaped beam spot on a wafer 1. The cylindrical lens 106 is used to reduce the size of an illumination light beam to match a receiving field of a line sensor (CCD or TDI) 205, which is coordinated with the wafer surface for image formation purposes. This also results in efficient use of illumination energy. The cylindrical lens 106 is equipped with an optical system which rotates to provide the same condensation for the front and rear sides of illumination when the light is illuminated from a direction having an angle of θ1 for major straight line group of a circuit pattern formed on the object under inspection. Instead of the cylindrical lens, a cone lens (conical lens) described, for instance, by Japanese Patent Laid-open No. 2000-105203 (equivalent to U.S. patent Ser. No. 09/362,135), may be alternatively used. A slit light beam, which is incident on the wafer surface at an inclination angle of α to the horizontal, bounces off the wafer's surface layer and scatters. A wafer 1 is inspected by running a relative scan over the stage system 300 and detection optical system unit 200. As indicated in FIG. 1, the detection optical system unit 200 mainly comprises a Fourier transform lens (which has a function as an objective lens) 201, an inverse Fourier transform lens (which has a function as an image forming lens) 202, and an image sensor 205, and is capable of inserting a spatial filter 2000 into a Fourier transform plane in an optical path. Alternatively, lens 201 may comprise an objective lens and a Fourier transform lens. Lens 202 may alternatively comprise an inverse Fourier transform lens and an image forming lens. In addition, the inverse Fourier transform lens 202 is vertically movable as indicated by an arrow mark so that the magnification can be changed.

Figure 26:
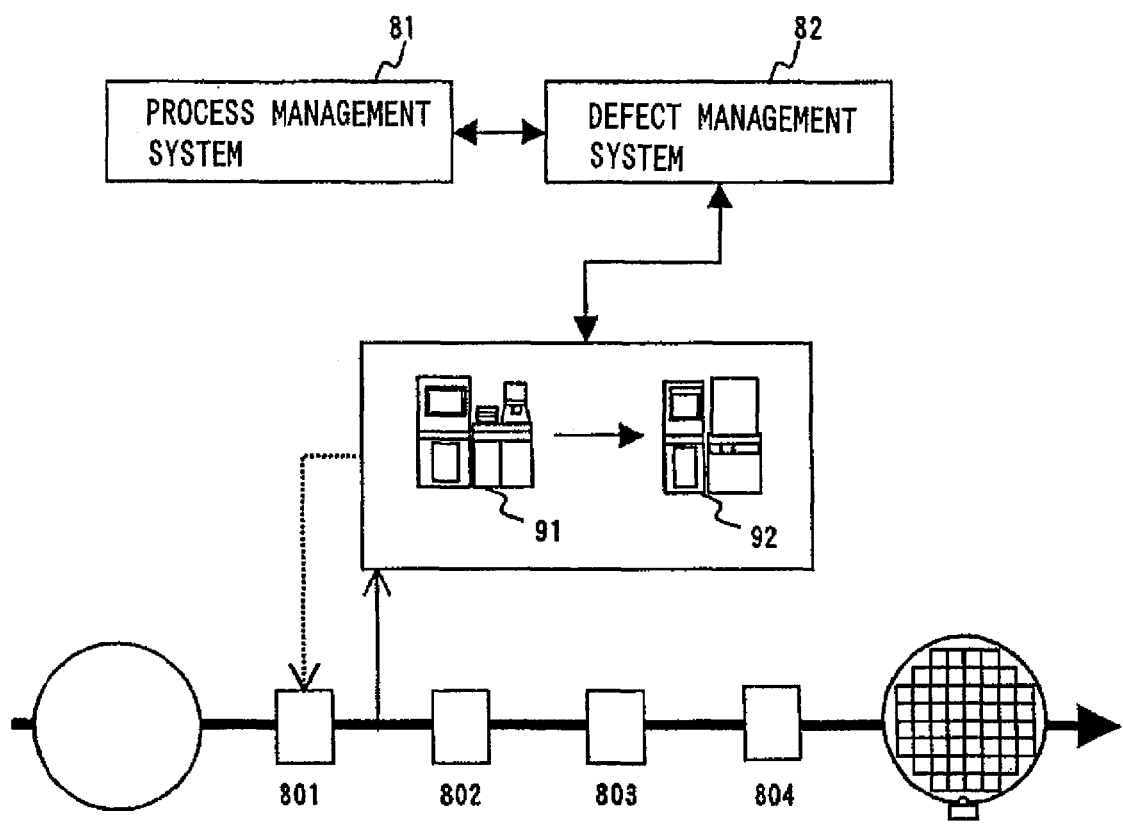
FIG. 26 is a block diagram showing one embodiment of improvement system in the yield of the semiconductor device.

Further, an optical path branching device 601 such as a mirror or beam splitter and a Fourier transform plane observation optical unit 600 can be inserted into an optical path. The Fourier transform plane observation optical unit 600 is equipped with a convex lens 602 and a TV camera 605 for observing a pattern in the Fourier transform plane. The convex lens 602 is movable as indicated by an arrow mark so that images of the Fourier transform plane and wafer surface can be formed by the TV camera 605. The signal output from the TV camera 605 enters the arithmetic processing system 400. The detected light, which is derived from the wafer 1, is passed through the inverse Fourier transform lens 202 and optical path branching device 601, polarized by a polarizing plate 203, adjusted by a light intensity adjustment plate 204 to vary its intensity, and incident on the image sensor 205. The light is then converted into an electrical signal by the image sensor 205, and the resulting electrical signal enters the arithmetic processing system 400. Light diffractions generated from edges of repetitive circuit patterns of the wafer surface are condensed (interfered) into a condensed light pattern (an interference pattern) having regular pitch in the Fourier transform plane. A spatial filter 2000 is set according to the condensed light pattern (the interference pattern) so that the diffracted light generated from the edges of the repetitive patterns do not reach the image sensor 205. Meanwhile, it is known that a Fourier image of foreign matter (particle) or defect is not regular and distributes irregularly in the Fourier transform plane. As a result, the light scattered from foreign matter and defects is partly shielded by the spatial filter; however, its greater part reaches the image sensor 205. Thus, by setting the spatial filter 2000 according to the condensed light pattern in the Fourier transform plane of the detection optical system unit 200, since the greater part of the scattered light of foreign matter and defects is received by the image sensor 205 so that the scattered light (the diffracted light) of the circuit pattern is removed, it becomes possible to detect the foreign matter/defect in high sensitivity by improving a S/N ratio. Since the detection lens of the detection optical system unit 200 is provided with a zoom optical system or an objective lens selector mechanism, it is possible to change the detection magnification. Since a detection pixel size (when they are converted to equivalent values for the wafer surface) becomes small in high magnification mode, it possible to detect the minute foreign matter/defect at a high sensitivity by improving the S/N ratio. However, the inspection speed is low because the detection pixel size are small. On the other hand, by enlarging the detection pixel size in a low magnification mode, inspection speed becomes early and, as a result, it is possible to inspect many wafers within a predetermined period of time. Since a plurality of magnification modes are available, it is possible to use the modes selectively to conduct a low-magnification, high-speed inspection on a product/process to which loose design rules are applied, and a high-magnification, high-sensitivity inspection on a product/process to which severe design rules are applied. The signal acquired by the image sensor 205 is subjected to data processing within the arithmetic processing system 400 to output a foreign matter/defect candidate. The result of foreign matter/defect detection is stored as electronic data on a recording medium within the apparatus or in a defect management system 82 as shown in FIG. 26 in the network-connected server unit.

A wafer ID (kind name, process name) and its recipe are entered in a recipe management system (not shown) within the server unit. As described later, the recipe contains an illumination light intensity value, illumination polarized light setting, illumination irradiation angle α setting for horizontal surface, illumination irradiation direction θ1 setting for the layout directions of the chips, detection visual field size, selected spatial filter data, and detection polarized light setting. A production line management system (not shown) within the server unit displays data to indicate whether the apparatus is conducting an inspection or on standby and indicate what is flowing on a production line. The defect management system 82 manages and displays the inspection result of the previous process.

The stage system 300 uses a stage controller 306 to control an X-stage 301, a Y-stage 302, a Z-stage 303, and a θ-stage 304 for the purpose of placing the wafer 1 in a specified position and at a specified height.

The foreign matter/defect inspection result displays on the monitor 500.

The scattered light from a wafer 1 passes the Fourier transform lens 201, and it is constituted so that the image of the wafer may image to the image sensor plane. The scattered light generated from the repetition pattern has a periodical light intensity distribution. Therefore, the diffraction image according to a repetition pitch of a pattern is imaged on the Fourier transform plane of a lens 201. On the other hand, since light intensity distribution of scattered light generated from the defect generally consists of random frequency components, the image of the scattered light does not image on the Fourier transform plane. So, by shielding the diffraction light generated from the repetition circuit pattern on a wafer 1 with the space filter 2000, the great portion of scattered light generated from the circuit pattern can be shielded, and, on the other hand, the great portion of scattered light generated from the defect can be passed. On this result, the scattered light from the circuit pattern is removed and the scattered light from the defect is only imaged on the image sensor 205, and it becomes possible to acquire the signal of the defect by the high S/N ratio.

Now, since the shielding plate is the purpose to shield the diffraction light, it is necessary to make widths of shielding portion of the shielding plate larger than widths of the diffraction light. Moreover, since the size of the opening of the Fourier transform plane is limited size decided by the design of a lens, the maximum number of spatial filters become settled by (Fourier transform plane opening diameter)÷(filter width). Since the filter which had width large enough compared with the width of the diffraction light was used from the problem of machine accuracy with conventional equipment, there were few numbers of the shielding plate. Therefore, this spatial filter with few numbers of the shielding plates cannot shield only the diffraction light of the repetition circuit pattern below 5 mm pitch on the wafer. Consequently, the diffraction light generated from the patterns of SRAM area, CCD circuit and a liquid crystal circuit on where the pattern pitch are large, could not shield only a part of the diffraction light.

In the present invention, it made it possible to position with high precision by changing structure of the spatial filter. It made it possible to become possible to narrow filter width, to use many numbers of filters, and to shield diffraction light generated from repetition pattern below 25 mm pitch by it.

Figure 2:
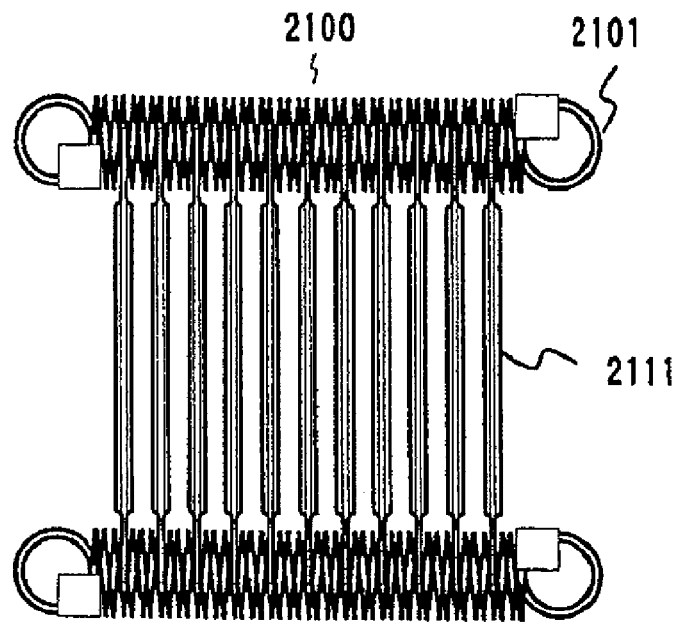
FIG. 2 is a front view showing 1st embodiment of a spatial filter (an object using a plurality of shielding plates and two springs of right wind)

FIG. 2 is shown a 1st embodiment 2100 of a shielding mechanism (a spatial filter). A plate 2111 is soldered to helix springs (clockwise twining spring-clockwise twining spring) 2101. This uses expanding and contracting with sufficient accuracy according to the law of a hook within the limits of elastic modification of a spring. If the shielding material 2111 is attached in the portion to which two springs 2101 correspond, the pitch of a filter can be changed with sufficient accuracy by making two springs 2101 expand and contract simultaneously. When shown in FIG. 2, two springs 2101 are constituted by a clockwise twining spring and a clockwise twining spring.

Soldering, adhesion material, welding, etc. can be considered as the technique of attaching (joining) the shielding material 2111 to the spring 2101. Although it can weld when the filter (the shielding material) 2111 and the spring 2101 are thick, when the filter 2111 and the spring 2101 become thin, in case it is welding, the attachment becomes difficult in order that the filter or the spring may melt. Therefore, when the filter 2111 and the spring 2101 become thin, solder and adhesives are good.

FIG. 4 is a figure showing what created the shielding plate 2111 in the state with frame 2110 using etching. A frame 2110 will be separated and removed after attaching the shielding plate 2111 to the spring finally. It is easy to solder the way whose thickness of an attachment part of the shielding plate is the almost same thickness as the diameter of the spring. Moreover, since the thickness of the shielding plate 2111 is decided from the condensed diameter of the diffraction light, and the machine accuracy of a filtering unit, the thickness of the shielding plate may differ between the attachment part and the shielding position. In such a case, in order to prevent concentration of the mechanical stress at the time of spring expansion and contraction, and the heat stress at the time of solder attachment, it is desirable to carry out curvature forming, as shown in an enlargement figure of FIG. 4.

On case of that the springs of the same wining direction are used as shown in FIG. 2, when the springs are made to expand and contract, the stress generated between the filters and the springs poses a problem. It is possible to negate the stress generated on both sides of the shielding material by combining a clockwise twining spring and a counterclockwise twining spring, and to further attain the high precision.

Figure 3:
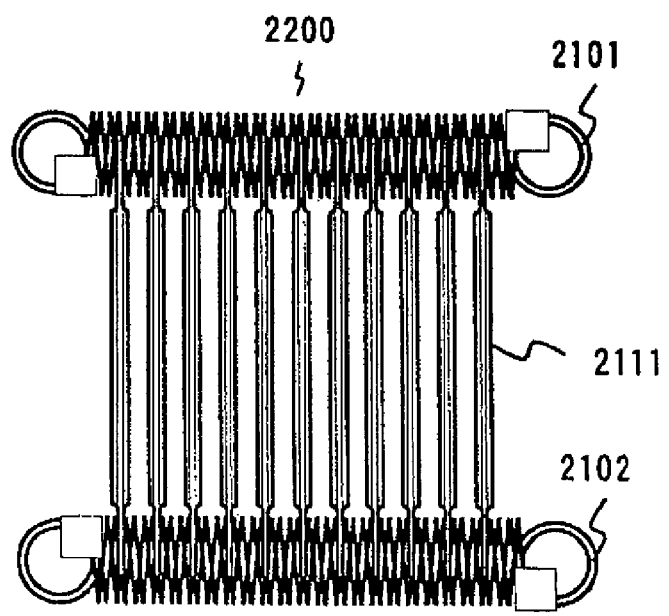
FIG. 3 is a front view showing 2nd embodiment of a spatial filter (an object being combined a shielding plate and two springs of right wind and left wind).
Figure 19:
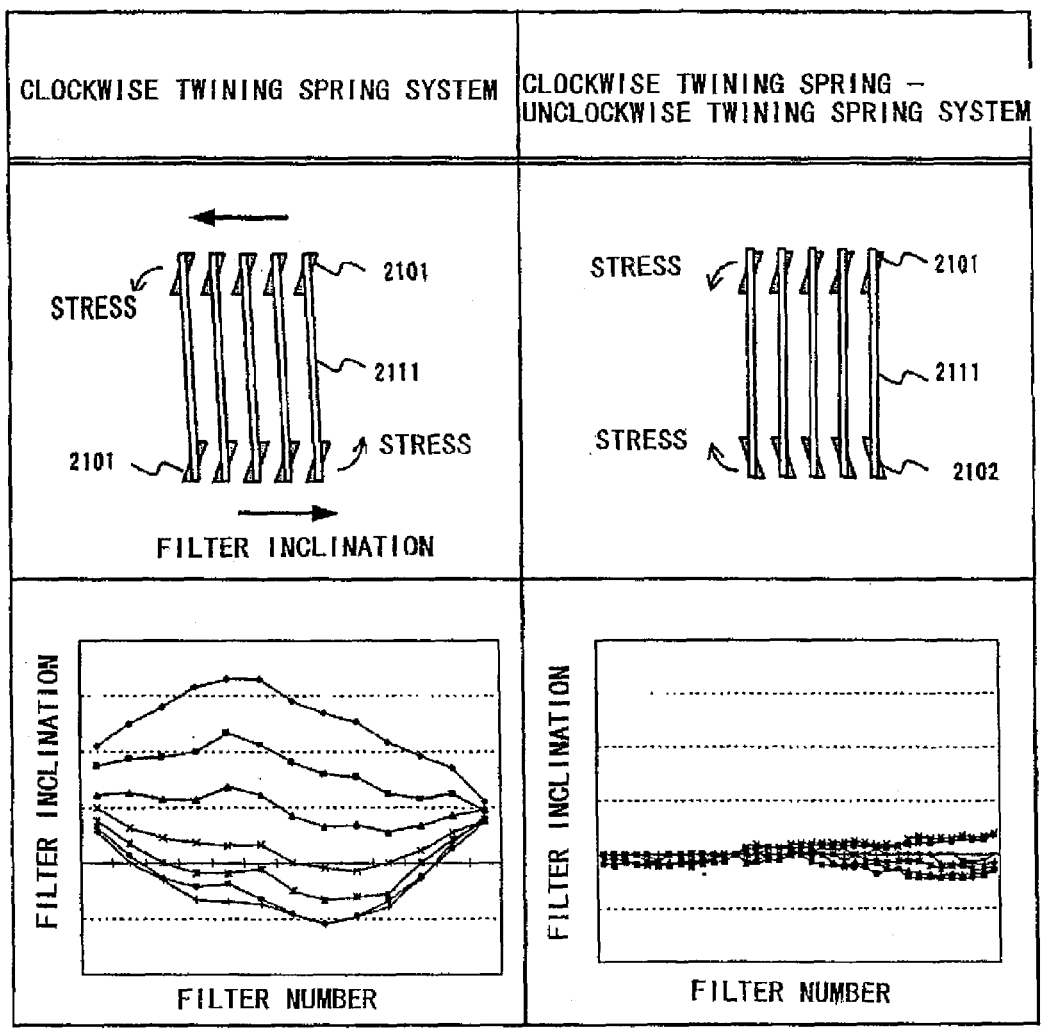
FIG. 19 is a figure which compares between composition of spatial filter of right wind spring system and composition of spatial filter of right wind spring and left wind spring combination system, and between filter inclinations on each of spatial filters.

FIG. 3 is a figure showing a 2nd embodiment 2200 of the spatial filter which combined the clockwise twining spring 2101 and the counterclockwise twining spring 2102. The graph of FIG. 19 is shown by plotting inclinations of the shielding plate 2111 for filter number when the filter springs make to expand and contract. Consequently, it can understand that the accuracy of a filter is improving by using the springs 2101, 2102 which are differ mutually the twining direction.

As the spatial filter, it is possible to use a transmission type liquid crystal 2300 and a micro-mirror array device 2400, etc. besides the combination of the springs and shielding material.

Figure 5:
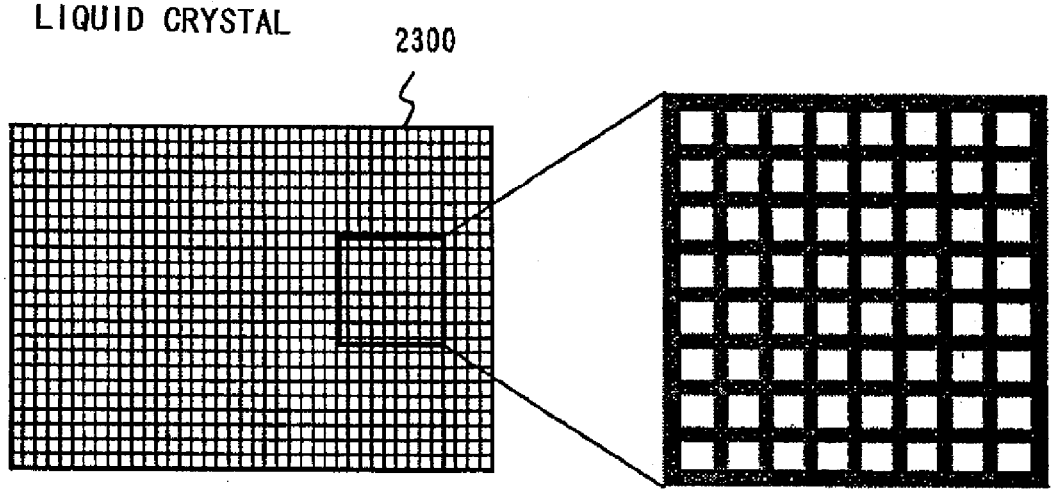
FIG. 5 is a front view showing 3rd embodiment of a spatial filter (transmission type liquid crystal).

FIG. 5 is shown the transmission type liquid crystal 2300 which is a 3rd embodiment of the spatial filter. Since the transmission and the shielding of light can be chosen by setting up ON and OFF for every pixel, the flexibility of shielding pattern generation becomes high compared with the above spring-type spatial filter. Generally, although the liquid crystal device will fall off light amount since polarization is used, the measure is possible for the liquid crystal device by raising the intensity of illumination light.

Moreover, generally, as shown also in FIG. 7, since the liquid crystal device has a drive circuit for every pixel, it has the problem that the rate of opening is low. As the lowness of the rate of opening causes the fall of transmission rate and the diffraction phenomena in the lattice of the liquid crystal pixel, it is desirable to use a liquid crystal device that the rate of a opening is high as much as possible (at least 60% or more). On the other hand, when it thinks from a viewpoint of a shielding function, the transmission rate at the time of shielding has lower possible desirable one. Although the contrast of a liquid crystal device is defined by generally taking the ratio of the transmission light amount at the time of transmission and the transmission light amount at the time of shielding, it is desirable that the value of the contrast is 800:1 or more.

Figure 6:
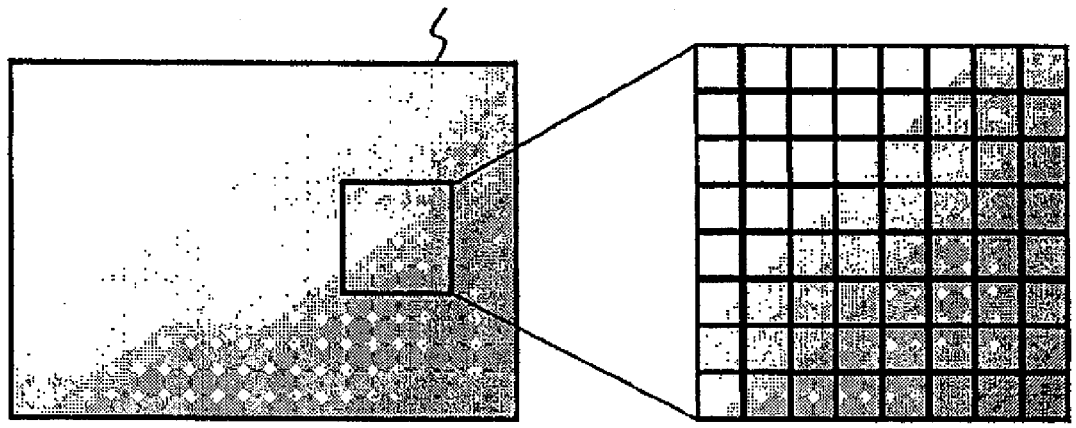
FIG. 6 is a front view showing 4th embodiment of a spatial filter (micro mirror array device).

FIG. 6 is a micro-mirror array device (a digital micro-mirror device (DMD)) 2400. Since the micro-mirror array device is generally 80% or more of high opening rate, the attenuation of light amount and the influence of diffraction in the lattice of the liquid crystal pixel, are low than the transmission type liquid crystal device. Consequently, the micro-mirror array device 2400 is desirable as the spatial filtering device.

Figure 8:
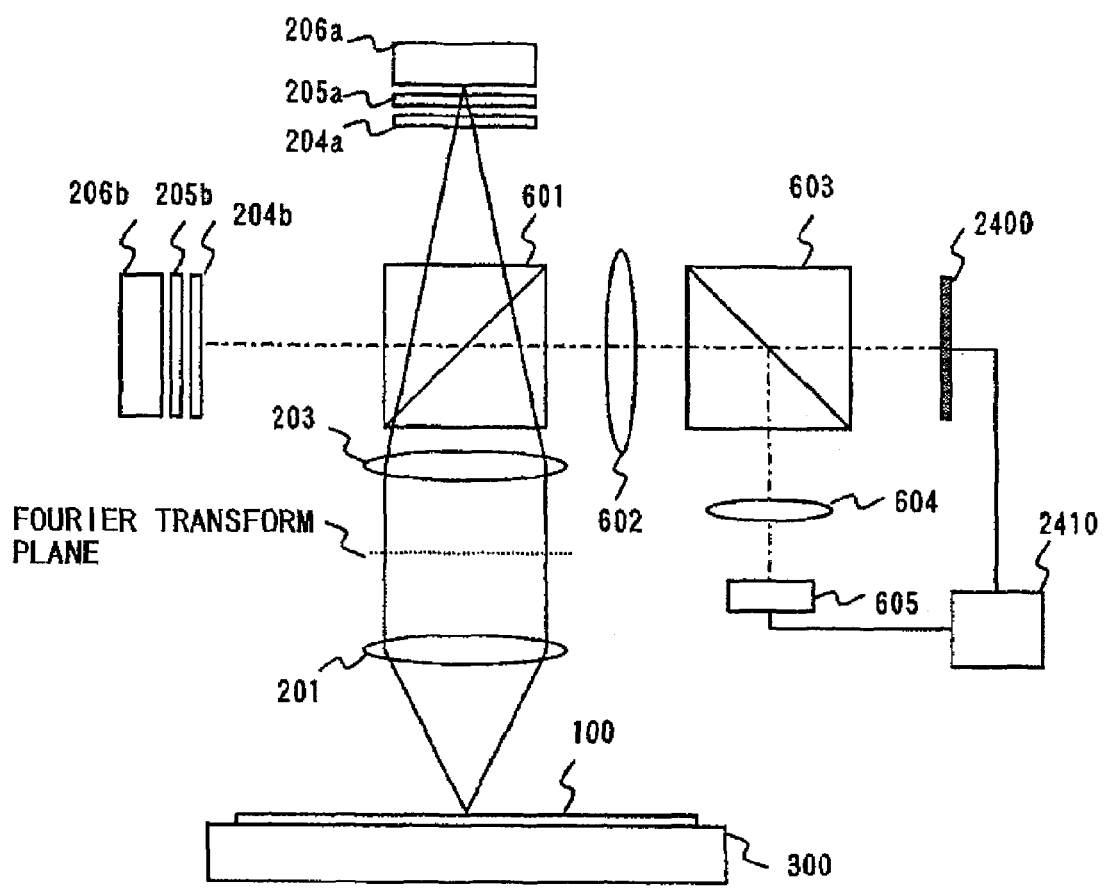
FIG. 8 is a front view showing an outline composition of an inspection apparatus on case of using the micro mirror array device as a spatial filtering unit.

FIG. 8 is the composition of the inspection apparatus at the time of using the micro-mirror array device 2400 as the spatial filter. The mechanism 601 which branches light path in the middle of an optical system is offered, and it has the sensor 605 which observes the spatial filter plane simultaneously. A shielding pattern is generated based on the picture of the Fourier transform plane taken in by the sensor 605, and many micro-mirrors 2400 is driven by a control unit 2410 which controls the micro-mirror array 2400. Diffraction lights which want to shield at this time are reflected in the direction which cannot receive on sensor 206b by the micro-mirror array 2400. The light which were not shield are reflected as it is by the mirror array 2400, and the light are taken in by sensor 206b. When the image sensor 206b receives diffraction lights generated from a defect, the spatial filter 2000 put on the Fourier transform plane will be removed.

Figure 9:
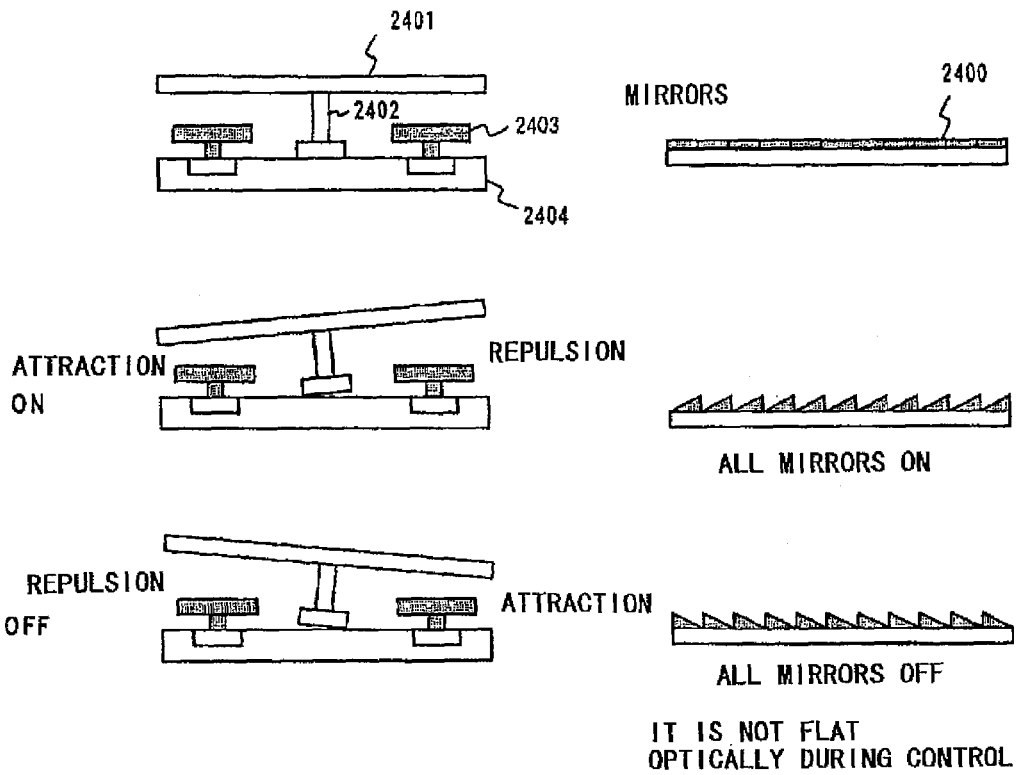
FIG. 9 is a front view showing 1st embodiment of the micro mirror array device.
Figure 10:
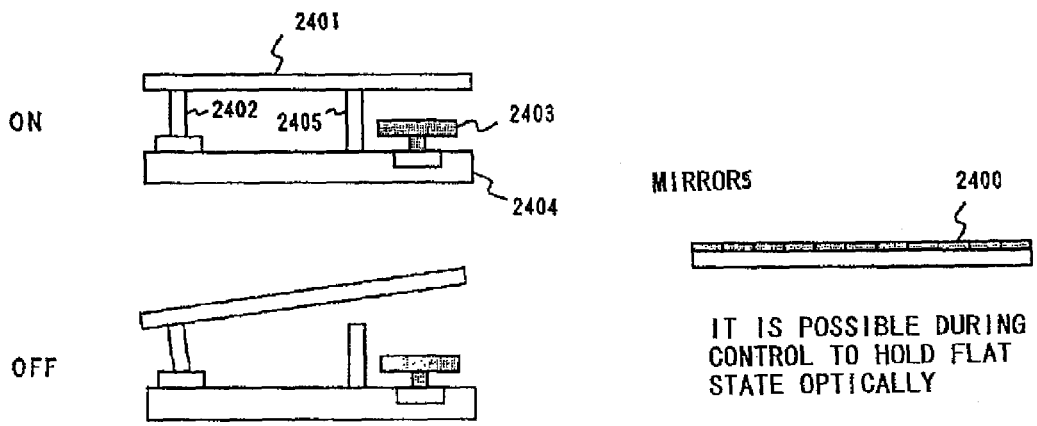
FIG. 10 is a front view showing 2nd embodiment of the micro mirror array device.

Moreover, FIG. 9 and FIG. 10 illustrate the section of two sorts of micro-mirror arrays. The micro-mirror array 2400 is the microelectronics device (DMD) made by being with the semiconductor process etc. A micro-mirror 2401 supported to a support 2402 being provided on a base 2404 is driven by electrostatic attraction and repulsion with electrode 2403 being provided on the base 2404. When the system of FIG. 10 which can keep optically a flat state by contacting to contact member 2405 combines with an image optical system 201, 203, 602, image accuracy becomes high and is desirable.

Figures 14, 15:
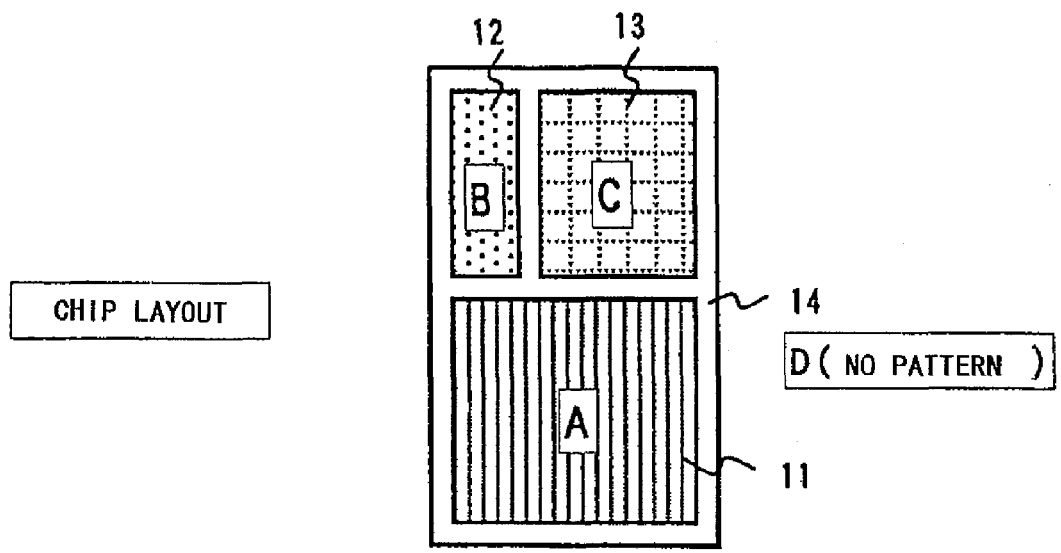
FIG. 14 is a figure showing a tip (a die) layout.
FIG. 15 is a diagram which compares diffraction patterns on each tip area with optimal shielding patterns.

As shown in FIG. 14, as for the semiconductor, the wiring pattern changes with the functions also in the tip (die). Therefore, the diffraction pattern and the optimal shielding pattern corresponding to it differ for each area A~D as shown in FIG. 15. Numerical number 11 is shown a area A. Numerical number 12 is shown a area B. Numerical number 13 is shown a area C. Numerical number 14 is shown a area D without a circuit pattern.

Figure 16:
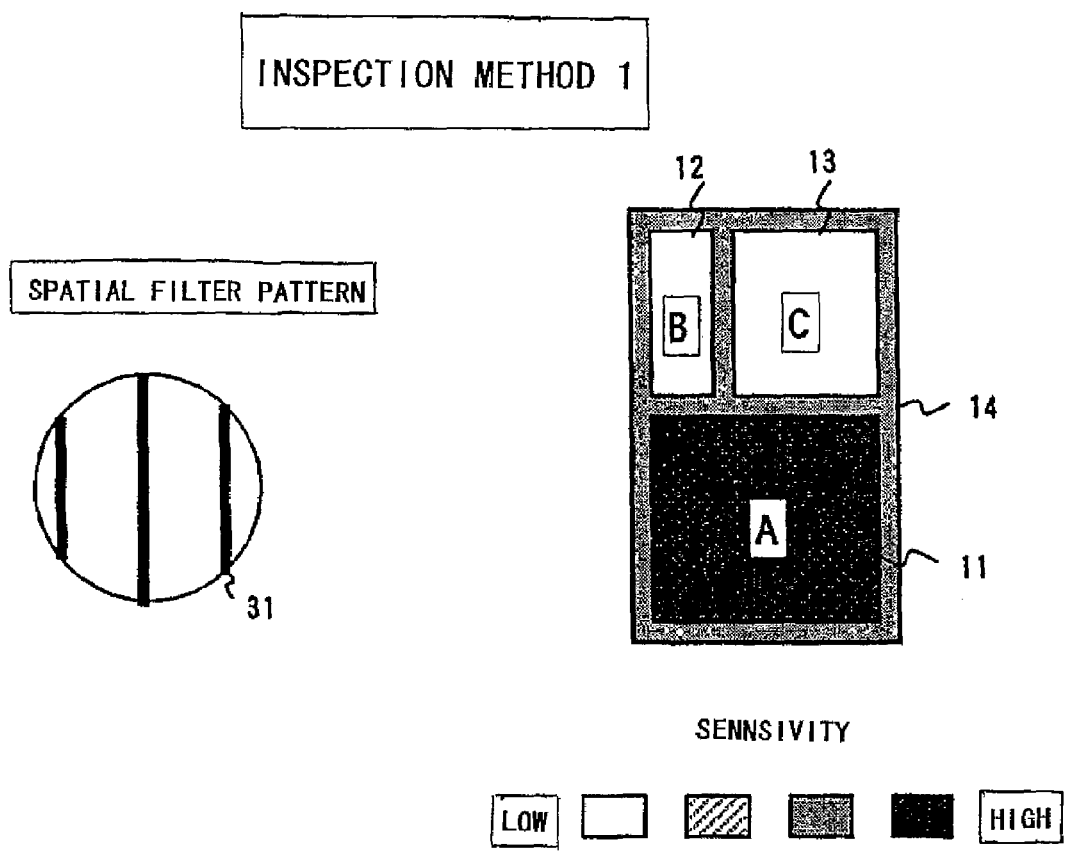
FIG. 16 is a figure showing 1st embodiment of the inspection method.

Although FIG. 16 is a 1st embodiment of the inspection method, it is a method of inspecting a wafer by matching (aligning) the optimal shielding pattern of the spatial filter with the circuit pattern of the largest area A (11). Although this method can be inspected in high sensitivity in the area matching (aligning) the filter, other area has the subject that sensitivity will become low.

Figure 17:
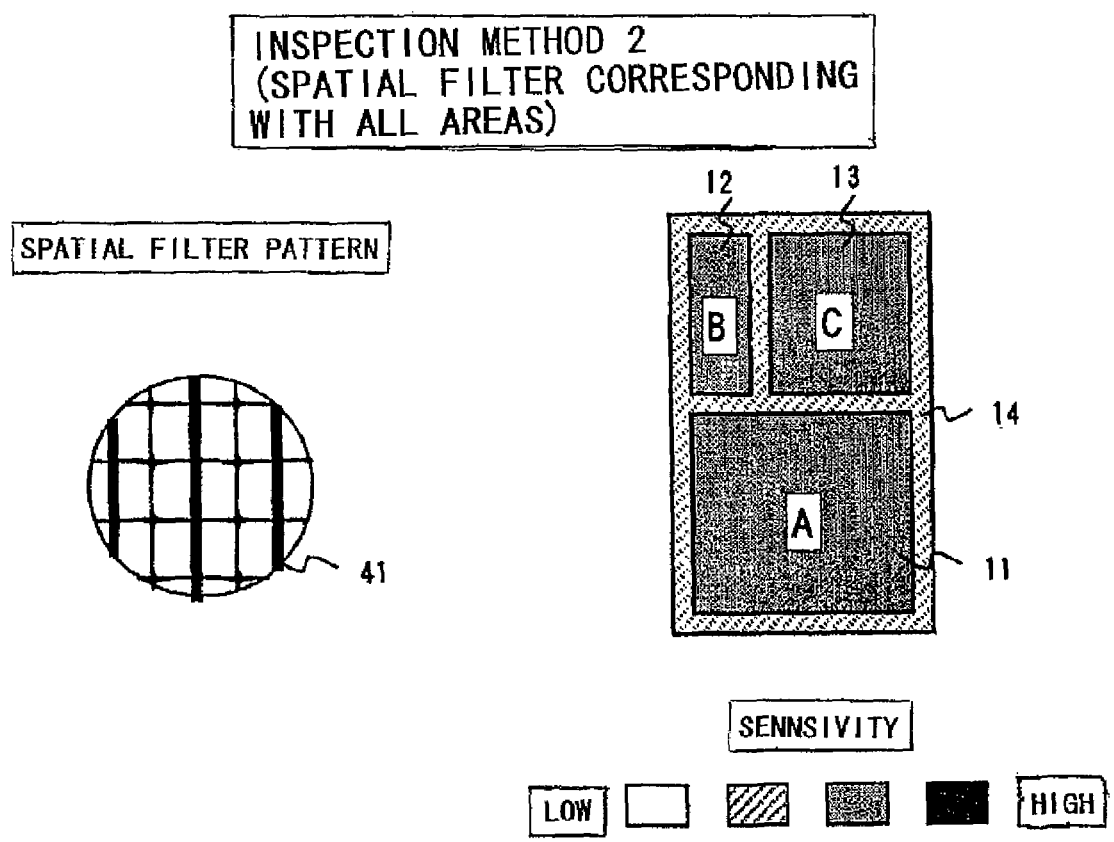
FIG. 17 is a figure showing 2nd embodiment of the inspection method.

FIG. 17 is a method of inspecting by using a shielding pattern, the shielding pattern 41 being generated by merging (taking logical sum) diffraction of each pattern. Although it can inspect evenly regardless of the form of patterns if it is this system, the subject referred to as being unable to perform inspection of high sensitivity occurs.

Figure 18:
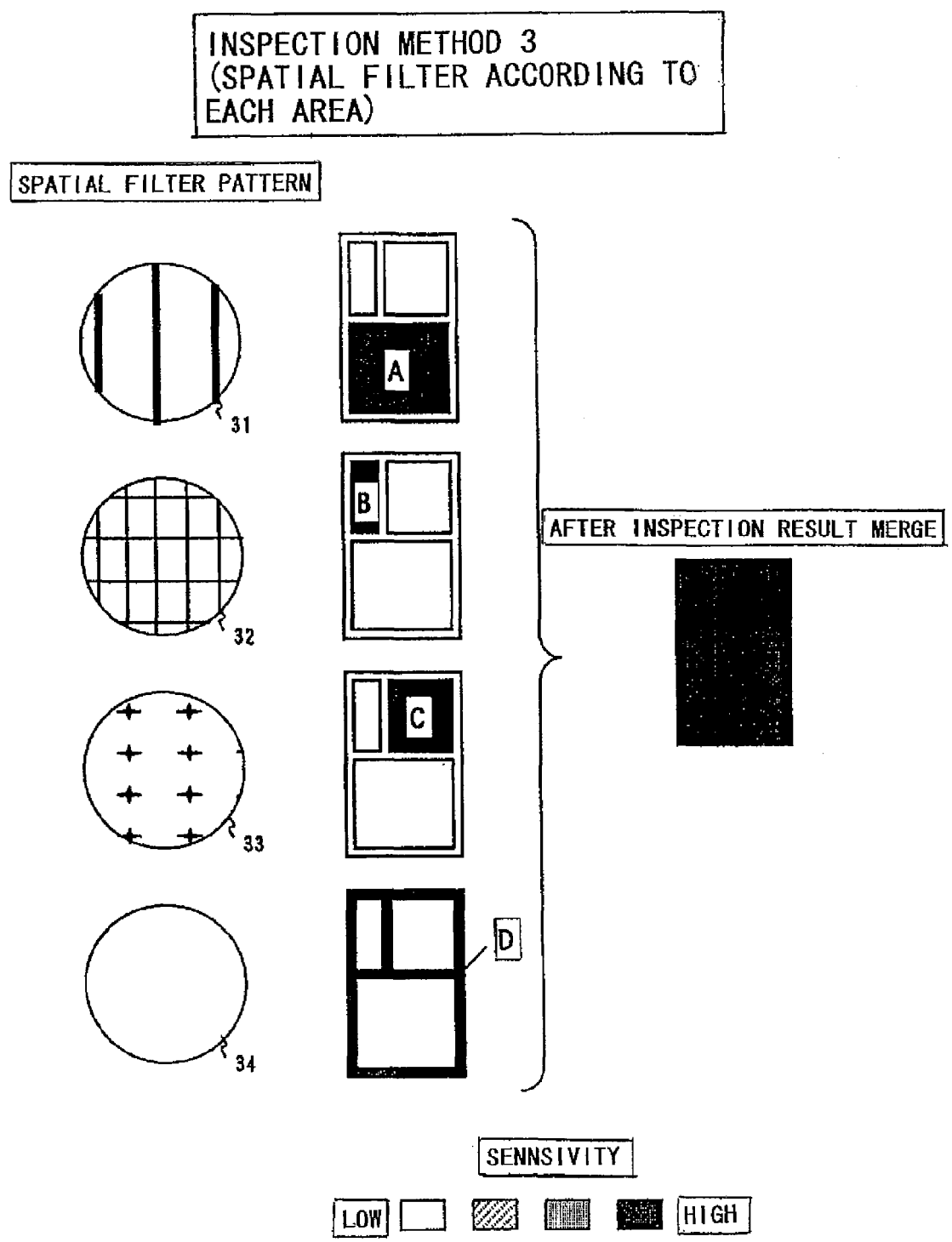
FIG. 18 is a figure showing 3rd embodiment of the inspection method.

FIG. 18 is a method of inspecting two or more times by matching the patterns 31~34 of the spatial filter for each pattern A~D. This method can perform inspection of high sensitivity for any area by merging two or more times of inspection results. However, it is a subject that throughput falls in order to carry out two or more inspection. When considering the strategy of an efficient inspection using the inspection apparatus with high enough sensitivity for the process of a semiconductor, the inspection method of FIG. 17 is desirable. Moreover, in a case of that it is need to inspect a specific pattern in high sensitivity in the time of introduction of a new process and starting of a production line etc., the inspection method of FIG. 16 or 18 is desirable.

Figure 11:
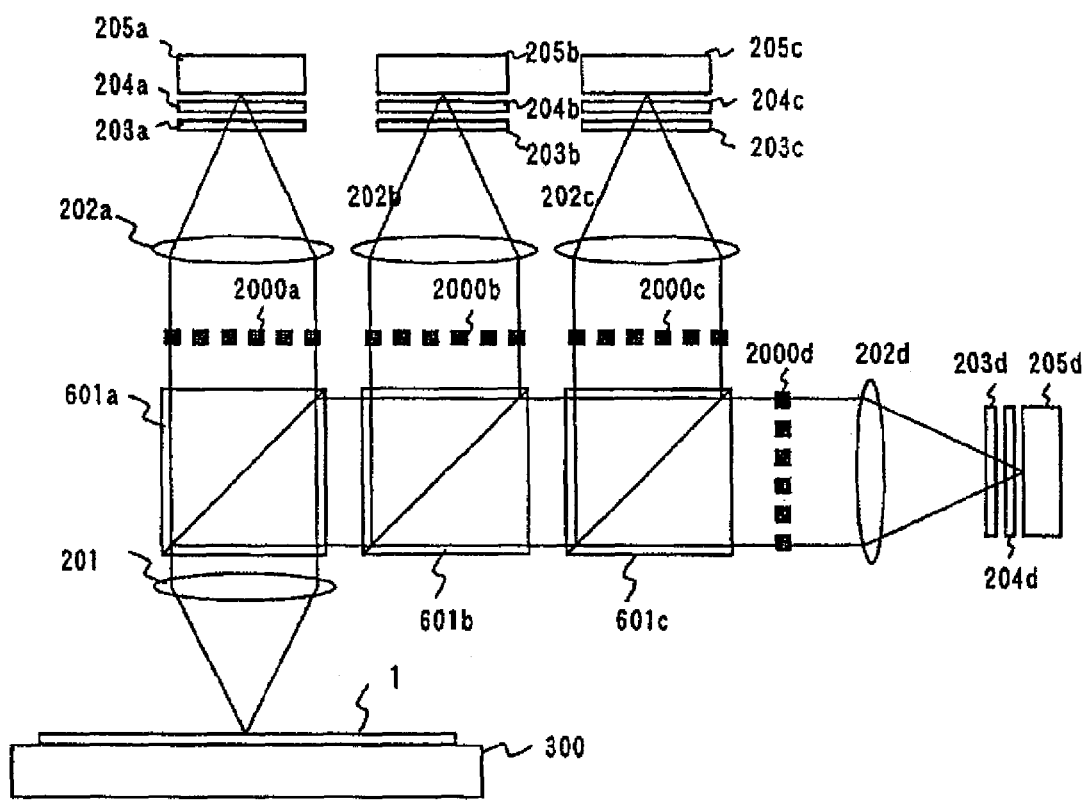
FIG. 11 is a front view showing an outline composition of an inspection apparatus which a plurality of spatial filtering units are used.
Figure 12:
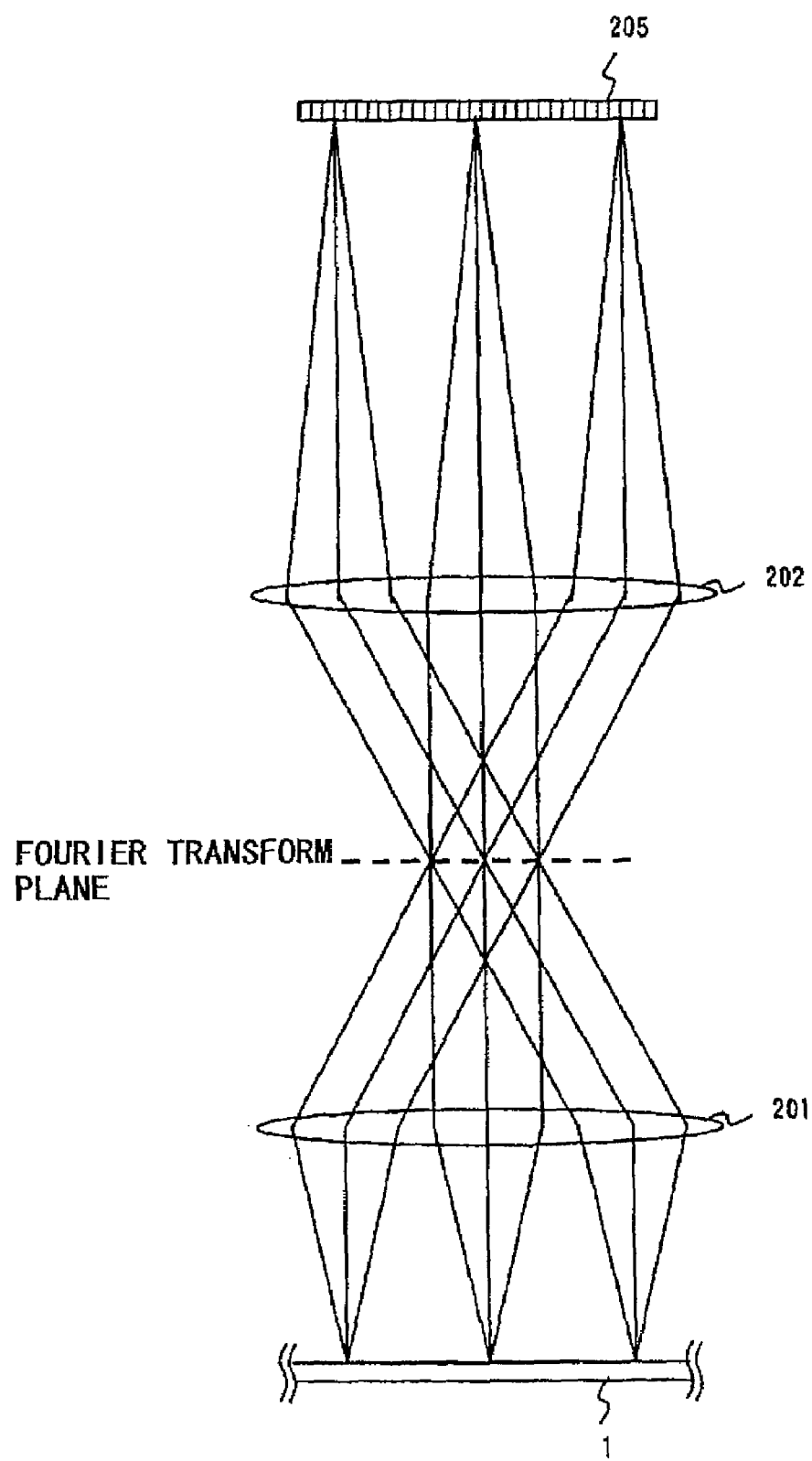
FIG. 12 is a front view of a Fourier optical system showing an optical path diagram of the Fourier optical system.
Figure 13:
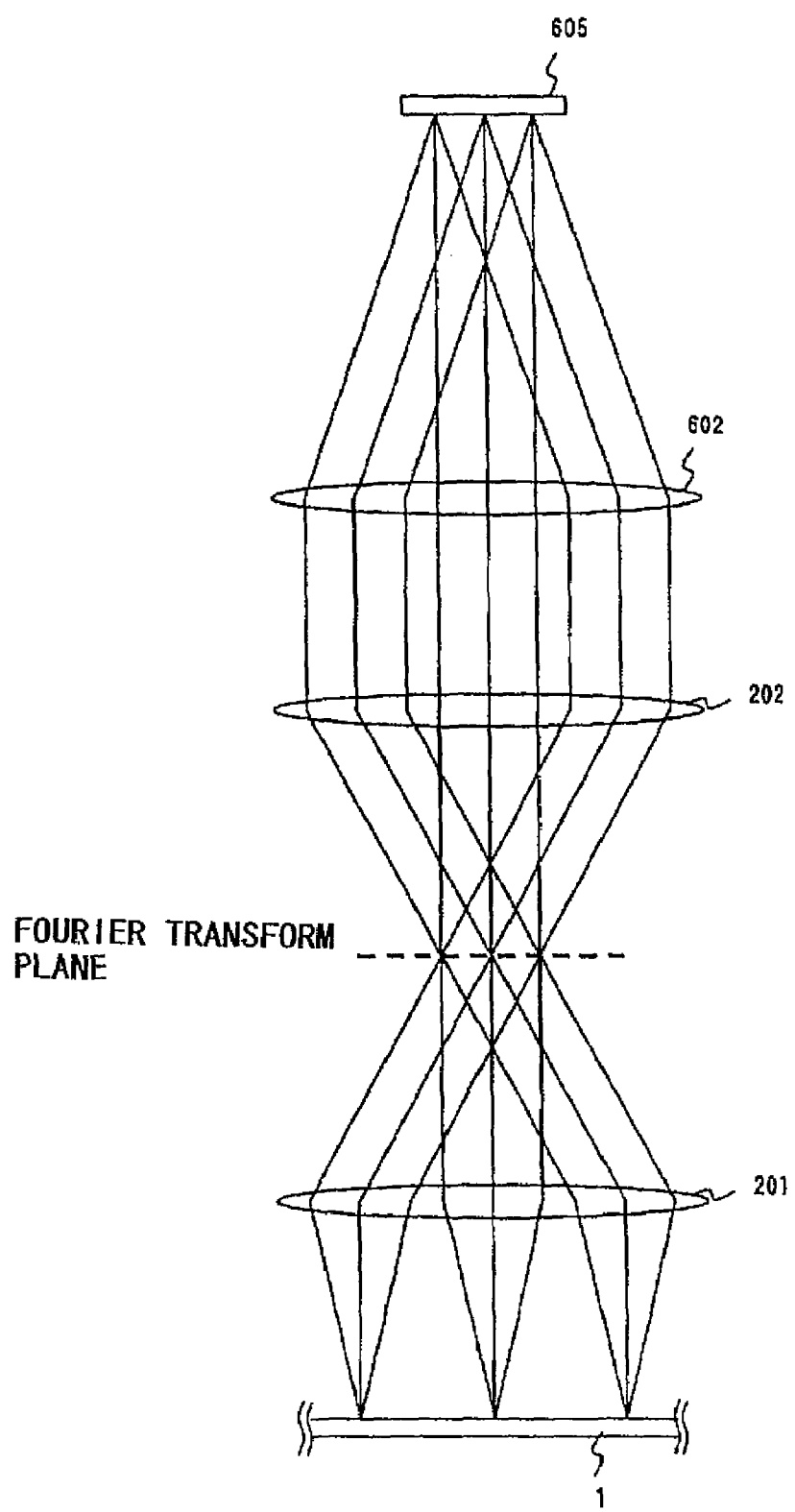
FIG. 13 is a front view of a Fourier optical system showing an optical path diagram of an optical system which observes a Fourier transform plane.

FIG. 11 is one embodiment of inspection apparatus equipped with two or more spatial filter units 2000a~2000d, and if amount of illumination light is sufficiently obtained, it will become possible to inspect at high sensitivity and the high throughput for all areas with this system. Numerical number 601a~601c are branched optical systems. Numerical number 201 is a Fourier transform lens (which has a function as an objective lens). Numerical number 202a~202d are an inverse Fourier transform lens (which has a function as an image forming lens). Numerical number 203a~203d are a polarizing plate. Numerical number 204a~204d are a light intensity adjustment plate. Numerical number 205a~205d are a line image sensor (CCD or TDI). FIG. 12 shows a Fourier optical system 201, 202. FIG. 13 shows the optical system 600 (602, 605) which observes the Fourier transform plane.

FIG. 20 is a figure showing embodiment of a scanning method when taking in diffraction image for one chip, on a case of setting up shielding patterns of the spatial filter automatically. As shown in FIG. 21, since the pattern of diffraction light is decided with the circuit pattern A~D of the chip, it turns out that it changed from predetermined pattern to another pattern on a chip by seeing (observing) change of the diffraction pattern 21~24 with the optical system 600 (602, 605). That is, the layout information on a chip will be known by paying one's attention to change of the diffraction pattern 21~24. Paying attention to this point, it becomes possible to determine any spatial filter should be used on certain area, by being taken in the diffraction patterns for one chip and by investigating each diffraction pattern. In accordance with above mention, it becomes possible to set up a spatial filter automatically by combining image processing with taking in of the diffraction pattern for one chip.

Figure 22:
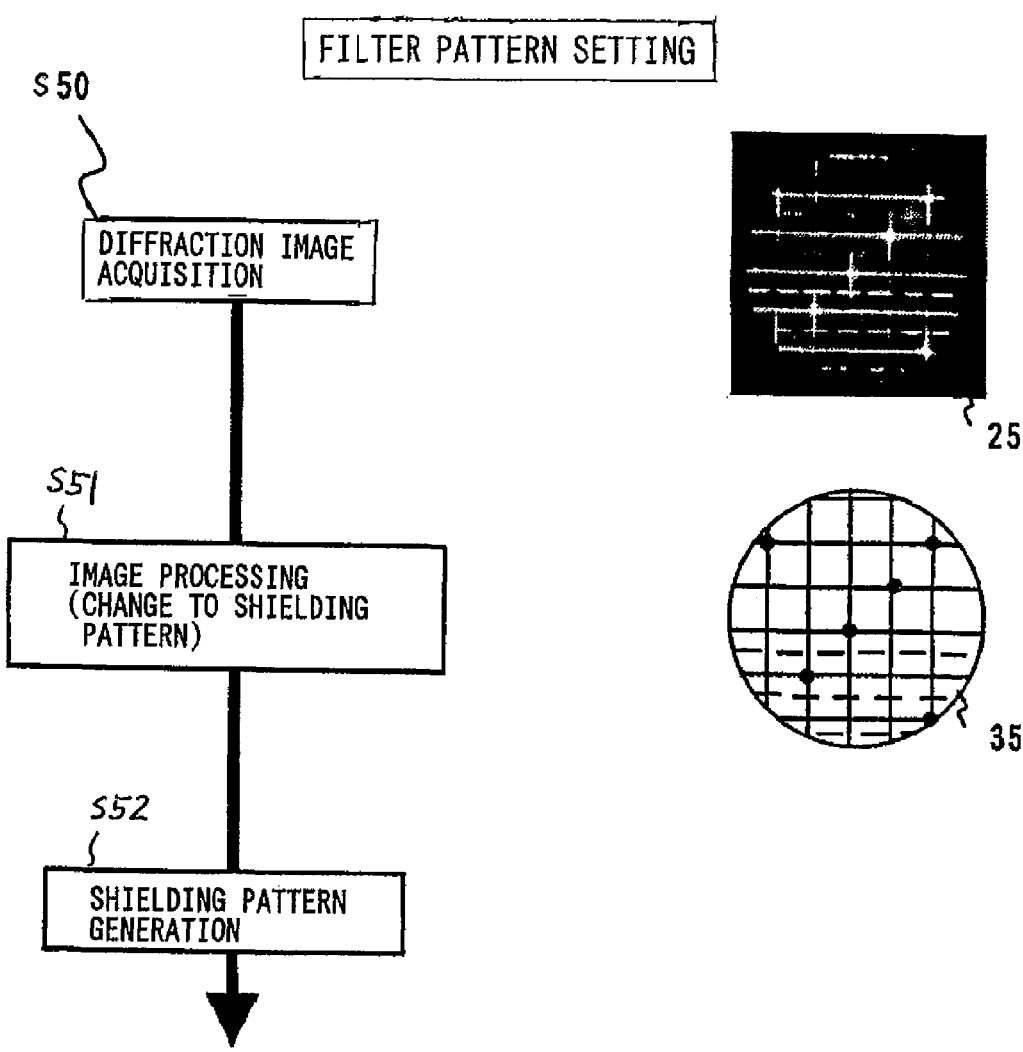
FIG. 22 is a figure showing one embodiment of setting method of the filter pattern.

FIG. 22 shows setting sequence of the spatial filter. The diffraction image 25 is acquired by observing design data, wafer pattern, or diffraction pattern directly (S50). Then, it becomes possible to generate the filter pattern should compute by generating the shielding pattern 35 based on the image processing (S51, S52).

Figure 23:
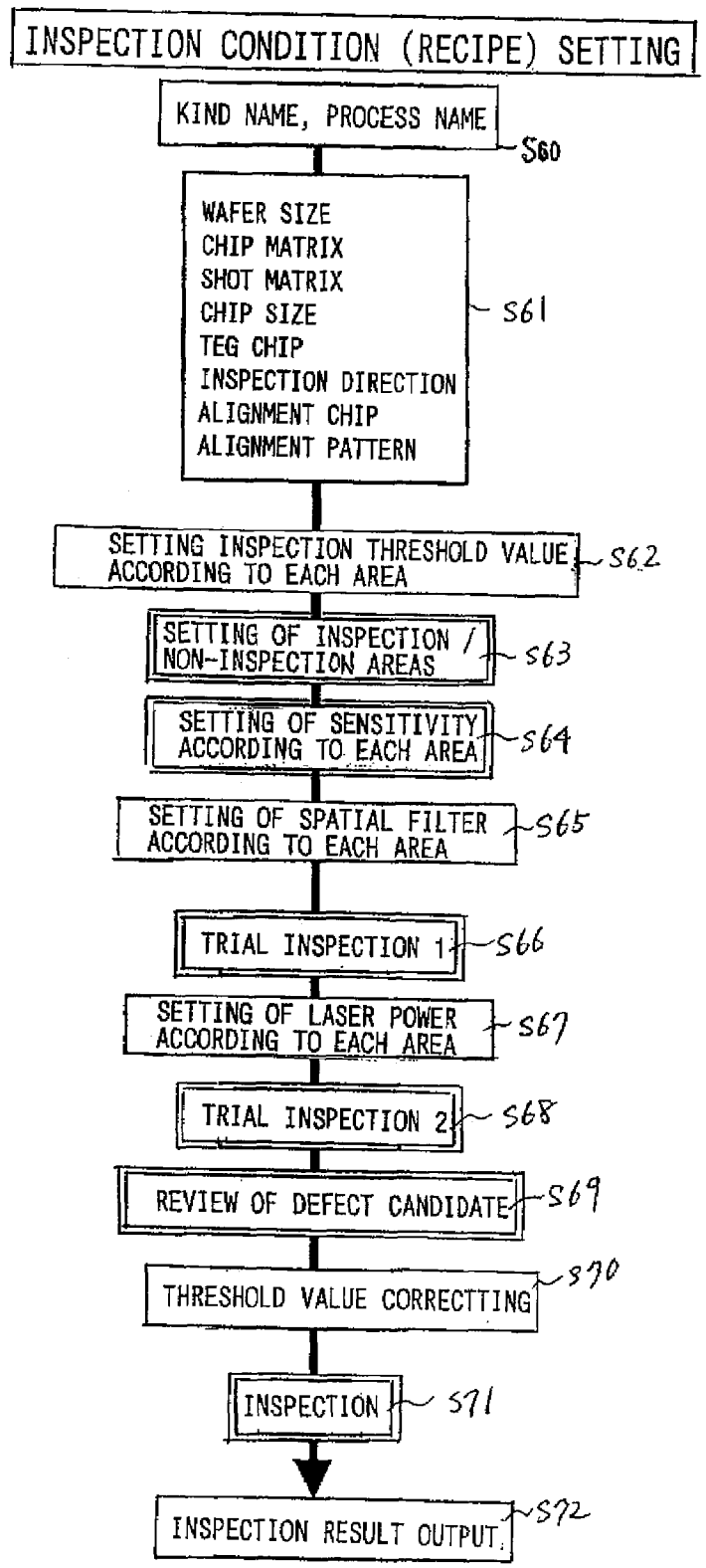
FIG. 23 is a figure showing one embodiment of setting method of inspection conditions.

FIG. 23 shows one embodiment of an inspection condition setting sequence in the arithmetic processing system 400 by using monitor 500. S60 is a step for inputting the kind name and the process name of a wafer including a chip. S61 is a step for inputting the information relating with the wafer, the information including wafer size, chip matrix, shot matrix, chip size, TEG chip, inspection direction (scan line) as shown in FIG. 20, alignment chip and alignment pattern. S62 is a step for setting up inspection threshold value according to each area A~D. S63 is a step for setting up inspection/non-inspection areas. S64 is a step for setting up sensitivity according to each areas. S65 is a step for setting up shielding patterns of the spatial filter according to each area A~D. Then, S66 is a step for performing a trial inspection 1. S67 is a step for setting up the laser power according to each area A~D based on the result of the trial inspection 1. S68 is a step for performing a trial inspection 2. S69 is a step for reviewing defect candidate detected by the trial inspection 2. S70 is a step for correcting the inspection threshold value set up by the step 62. S71 is a step for performing an actual inspection. S72 is a step for outputting the inspection result to the monitor 500 etc. There are described, for instance, by Japanese Patent Laid-open No. 2000-105203 (equivalent to U.S. patent Ser. No. 09/362,135).

Figure 24:
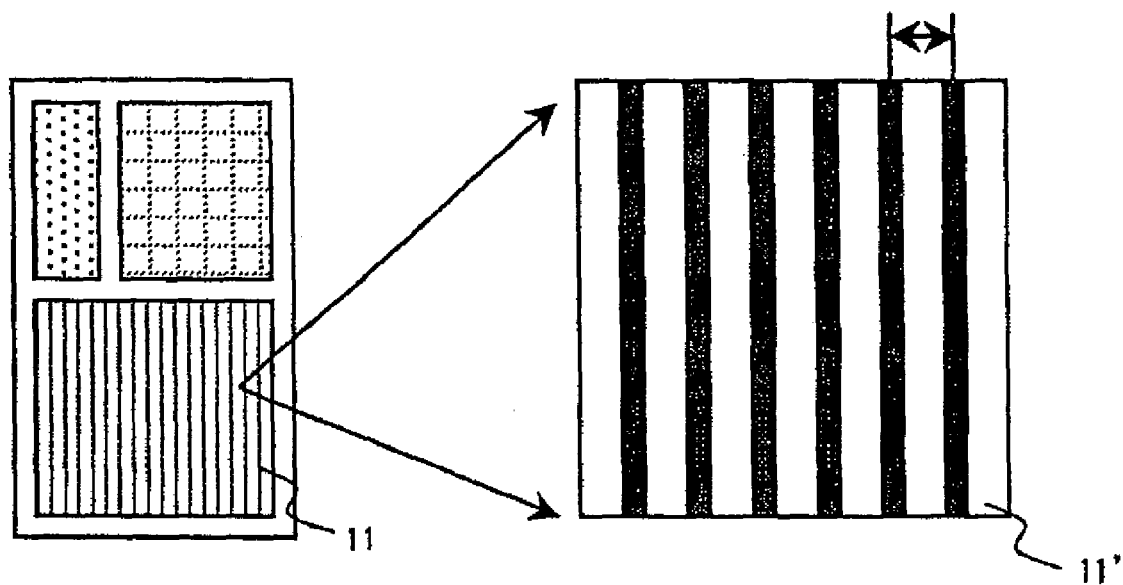
FIG. 24 is a figure showing another embodiment of setting method of the spatial filter.

FIG. 24 shows a method for calculating pitch (p) of diffraction light from a pattern pitch (d). p=(f·λ)/d However, f is focal length of the lens 201. λ is wave length of the light.

Figure 25:
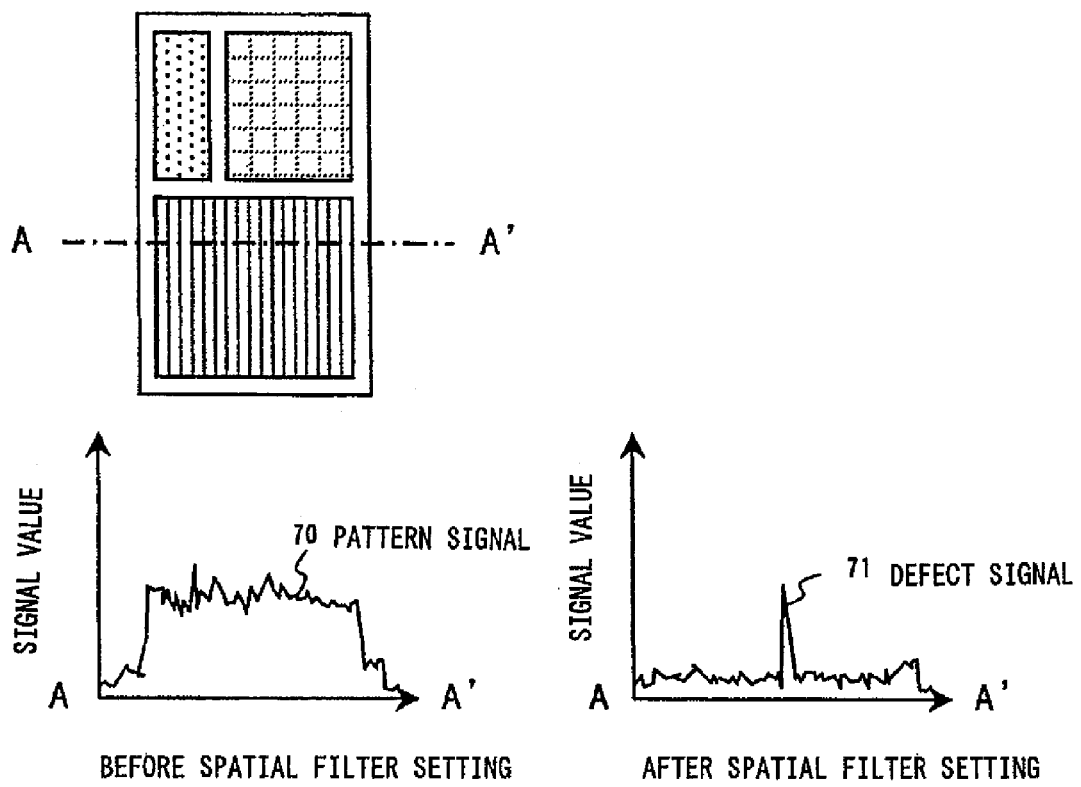
FIG. 25 is a figure showing pattern signals at the time of un-using it/at the time of using space filter.

FIG. 25 shows the signal intensity of the pattern at the time of using the spatial filter and at the time of not using it. At the time of not using it, defect signal cannot detect by separating from the pattern signal. However, as the signal of a pattern is decreased sharply by using the spatial filter, it becomes possible to acquire the signal of a defect with the high S/N ratio.

FIG. 26 shows the relation of an inspection apparatus 91, 92 and the manufacturing process of the semiconductor device. The wafer after specific process passage is inspected with an inspection apparatus 91. It becomes possible to apply feedback to the original process by identifying the details of a defect with review apparatus 62 etc. after the inspection has been performed by the inspection apparatus 91. It becomes possible to improve the yield of a semiconductor device by this repetition. Numerical number 81 is a process management system for managing the manufacturing process of the semiconductor device. Numerical number 82 is a defect management system for managing the defect information obtained from the inspection apparatus 91 and the review apparatus 62 etc.

As explained above, according to the present invention, in the technology of inspecting a minute circuit pattern using the image formed by irradiating white light, single wavelength light, and laser light, the foreign particles and the defect can be detected at high sensitivity by using highly precise spatial filtering.

What is claimed is:

1. A method for inspecting a specimen, comprising the steps of:
   irradiating and scanning a laser beam onto a specimen on which plural chips each having essentially the same patterns are formed;
   acquiring layout pattern information of the patterns formed on the chips by analyzing diffraction patterns of light diffracted from the specimen by the irradiation of the laser on the specimen; and
   inspecting the specimen by extracting defects on the chips by using said layout pattern information.

2. An inspection apparatus comprising:
   an illumination unit which irradiates light onto a specimen on which plural chips each having essentially the same patterns are formed;
   a detection optical unit which detects light from the specimen irradiated by the illumination unit;
   a stage unit which mounts the specimen and moves in a plane; and
   a processing unit which processes data required by the detection optical unit;
   wherein the processing unit acquires layout pattern information of the chips by using data of diffraction light pattern of the chips detected by the detection optical unit.

* * * * *